US005795545A

United States Patent [19]
Koripella et al.

[11] Patent Number: 5,795,545
[45] Date of Patent: Aug. 18, 1998

[54] INTEGRATED CERAMIC EXHAUST GAS SENSORS

[75] Inventors: Chowdary R. Koripella, Albuquerque; Adam D. Moya, Peralta; David Wilcox, Sr., Albuquerque, all of N. Mex.

[73] Assignee: Motorola Inc., Schaumburg, Ill.

[21] Appl. No.: 650,705

[22] Filed: May 20, 1996

[51] Int. Cl.$^6$ .................................................. G01N 25/22
[52] U.S. Cl. .......................... 422/94; 422/90; 422/95; 422/98; 73/23.01; 73/31.03; 73/31.05; 73/31.06; 338/24
[58] Field of Search ................. 422/90, 95, 98, 422/94; 73/23.01, 31.03, 31.05, 31.06; 338/24

[56] References Cited

U.S. PATENT DOCUMENTS

| | | | |
|---|---|---|---|
| 3,911,386 | 10/1975 | Beaudoin et al. | 338/34 |
| 4,007,435 | 2/1977 | Tien | 73/23.31 |
| 4,654,624 | 3/1987 | Hagan et al. | 338/34 |
| 4,697,165 | 9/1987 | Ishiguro et al. | 73/23.31 |
| 4,883,947 | 11/1989 | Morase et al. | 73/23.31 |
| 4,928,513 | 5/1990 | Sugihara et al. | 73/31.06 |
| 4,950,380 | 8/1990 | Kurosawa et al. | 204/406 |
| 5,034,107 | 7/1991 | Wang et al. | 204/153.14 |
| 5,064,693 | 11/1991 | Hayakawa et al. | 422/95 |
| 5,171,721 | 12/1992 | Nanataki et al. | 501/81 |
| 5,250,169 | 10/1993 | Logotheffis et al. | 422/98 |
| 5,329,806 | 7/1994 | McClanahan et al. | 73/31.05 |
| 5,334,350 | 8/1994 | Friese et al. | 73/31.06 |
| 5,367,283 | 11/1994 | Lauf | 422/90 |
| 5,397,442 | 3/1995 | Wachsman | 204/153.6 |
| 5,400,643 | 3/1995 | De-Angelis et al. | 73/31.06 |
| 5,451,371 | 9/1995 | Zanini-Fisher et al. | 422/95 |
| 5,460,711 | 10/1995 | Riegel et al. | 204/425 |
| 5,467,636 | 11/1995 | Thompson et al. | 73/23.31 |
| 5,562,811 | 10/1996 | Lenfers | 422/94 |
| 5,608,154 | 3/1997 | Kato et al. | 73/30.03 |
| 5,616,825 | 4/1997 | Achey et al. | 73/31.05 |

FOREIGN PATENT DOCUMENTS

| | | | |
|---|---|---|---|
| 048459 | 4/1979 | Japan. | |
| 0103045 | 6/1982 | Japan. | |
| 0028857 | 2/1986 | Japan | G01N 27/46 |
| 0030757 | 2/1986 | Japan | G01N 27/46 |
| 787973 | 12/1980 | U.S.S.R. | |

*Primary Examiner*—Jill Warden
*Assistant Examiner*—Sharidan Carrillo
*Attorney, Agent, or Firm*—Brian M. Mancini

[57] ABSTRACT

A multilayered ceramic integrated sensor 200 for monitoring auto exhaust gases is capable of existing in the relatively harsh environments of the exhaust stream of an internal combustion engine. The integrated sensor 200 may include discrete devices such as an oxygen sensor 104, a hydrogen sensor 206, an NO$_x$ sensor 208, and a carbon monoxide sensor 210. The device 200 may further include a temperature sensor 202 as well as total combustion calorimetric sensor 102. The multilayered ceramic integrated sensor may be fabricated from a plurality of layers of ceramic material disposed in stacked relationship with respect to one another.

15 Claims, 6 Drawing Sheets

INTEGRATED CERAMIC EXHAUST GAS SENSORS

TECHNICAL FIELD

This invention relates in general to ceramic multi-layered devices and more particularly ceramic automotive exhaust gas sensors.

BACKGROUND OF THE INVENTION

Automobile manufacturers have long sought to monitor the exhaust gases emitted from internal combustion engines. Monitoring the exhaust gases provides several useful benefits, including: determination of catalytic converter efficiency; measurement of total combustibles coming out of the catalytic converter; reduction in hydrocarbon emissions to meet state and federal emissions requirements; adjustment of the air/fuel ratio in the engine cylinders; and overall better performance of the internal combustion engine. The goals of measuring certain outputs are particularly important when considering that increasingly stringent state and federal requirements make the exhaust of certain components undesirable at best, and illegal at worst.

There have heretofore been several attempts to make silicon based hydrocarbon sensors for automotive applications. Most of these types of applications have related to micro machined calorimetric gas sensors. These types of devices have the advantage of being relatively small and hence possess low thermal mass, as well as being highly sensitive. However, such devices have not found widespread acceptance in the marketplace due to the fragile structure of the silicon from which the devices are made, reliability of the overall device, and susceptibility to carbon deposits resulting in poor device performance.

Similarly, ceramic materials have been investigated for use in such sensors though have been found undesirable or lacking. This is generally been due to the fact that such devices were of the ceramic bead type, resulting in relatively large thermal mass and hence poor device performance. Moreover, such devices have heretofore tended to be discrete individual devices. That is, multiple sensors for multiple applications have not been able to be readily incorporated into a single device. The best candidate for doing so heretofore would be silicon, though silicon suffers from the shortcomings mentioned hereinabove.

Accordingly, there exists a need for an integrated automotive exhaust gas sensor which allows for the measurement of numerous components in the exhaust gas. The device should be manufactured in a relatively robust medium which is inexpensive, highly accurate and which can be made into highly repeatable units. The device should also be substantially inert in that it should not react with the exhaust gases, or release toxic chemicals into the atmosphere.

DETAILED DESCRIPTION OF THE PREFERRED EMBODIMENT

While the specification concludes with claims defining the features of the invention that are regarded as novel, it is believed that the invention will be better understood from a consideration of the following description in conjunction with the drawing figures, in which like reference numerals are carried forward.

Figure 1:
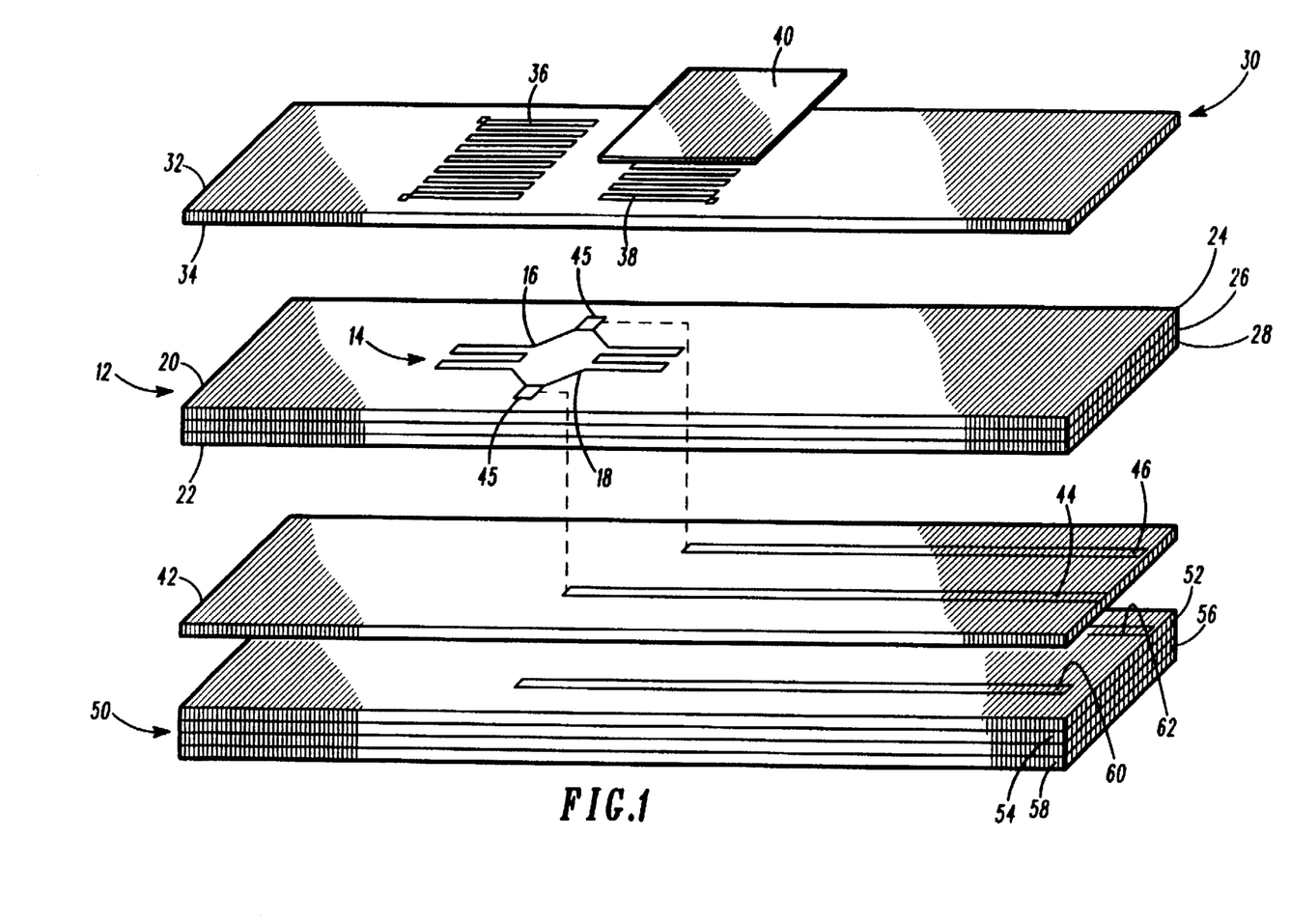
FIG. 1 is an exploded perspective view of a ceramic combustion calorimetric sensor in accordance with the instant invention.

Referring now to FIG. 1, there is illustrated therein an exploded perspective view of a multilayered ceramic, calorimetric combustion sensor 10 for an automobile exhaust system. The calorimetric total combustion sensor 10 comprises a first layer of ceramic material 12 upon which is deposited a first metallized pattern 14. The metallized pattern comprises first and second heating coils 16 and 18. The heating coils 16 and 18 are formed of metal patterns which are deposited on the ceramic layer material 12 in a manner well known in the art. In one preferred embodiment, the metallized pattern 14 is printed on the ceramic material 12 by means of screen printing.

The ceramic layer 12 may be fabricated of a plurality of layers of ceramic material arranged one atop the other in a stacked configuration. In this regard, the layer 12, whether a single or multiple layers of ceramic materials, is fabricated to include first and second major surfaces 20 and 22. The metallized pattern is therefore deposited on at least one of said first and second major surfaces, and in the embodiment of FIG. 1, is on first major surface 20.

As noted above, ceramic layer 12 may be fabricated of a plurality of layers of ceramic material. As shown in FIG. 1, ceramic layer 12 comprises three layers of ceramic material 24, 26, and 28. The ceramic materials which go into ceramic layer 12, making up layers 24, 26, and 28, may all be the same or alternatively may be fabricated of different materials so as to provide different desired characteristics. The materials of which ceramic layer 12 and indeed other ceramic layers used in the instant invention will be described in greater detail hereinbelow.

Operatively disposed immediately above ceramic layer 12, and specifically first major surface 20 is a second layer of ceramic material 30. Layer 30 includes first and second major surfaces 32 and 34 respectively. Disposed upon first major surface 32 of ceramic layer 30 are first and second conductive coils 36 and 38. The conductive coils 36 and 38 are fabricated of an electrically conductive material such as titanium, vanadium, chromium, nickel, tungsten, platinum, a nickel-chromium alloy, and combinations thereof. In one preferred embodiment, metallized pattern 14 and coils 36 and 38 are fabricated of platinum so as to make it easily co-fireable with the ceramic materials in layers 12 and 30. Alternatively, higher resistance materials such as tungsten and Ni-Cr alloys may be used for coils 16 and 18 and platinum for coils 36 and 38. The conductive coils are deposited on first major surface 32 of ceramic layer 30 by means of conventional deposition techniques such as, for example, screen printing. Second ceramic layer 30 is operatively disposed atop the first ceramic layer 12 such that conductive coil 36 is immediately atop heating coil 16, while conductive coil 38 is immediately atop heating coil 18. Deposited on one of the conductive coils is a layer of a catalytic material 40. As shown in FIG. 1, layer 40 is deposited on coil 38. In one preferred embodiment, the layer of catalytic material 40 is fabricated of a platinum or platinum alloy catalytic material. The platinum catalytic material maybe deposited atop conductive coil 36 in any of a number of known different methods, including, for example, screen printing.

Disposed immediately adjacent to first ceramic layer 12 is a third ceramic layer 42 which has disposed thereon a plurality of electrically conductive leads, 44 and 46. Electrically conductive leads 44 and 46 are provided so as to allow for input and output contacts at the edge of the combustion sensor which allow the combustion sensor to be electrically coupled to, for example, a power source or a processing means (not shown). Electrically conductive leads 44 and 46 are also electrically coupled to heating coils 16 and 18 so that an electric current may be run along said conductive leads 44 and 46 thereby causing coils 16 and 18 to heat. Conductive leads 44 and 46 make electrical contact with coils 16 and 18 through one or more filled vias 45 formed through ceramic layer 12. Said vias are filled with a conductive material similar to that used to fabricate the conductive leads 44 and 46. The conductive leads are preferably fabricated of the same type of materials as were described hereinabove with respect to coils 16, 18 and 36 and 38. Likewise, conductive leads are deposited upon ceramic layer 42 in similar manner.

Disposed immediately subjacent third ceramic layer 42 is a fourth ceramic body 50. Ceramic body 50 like first ceramic layer 12 may be fabricated of one or more layers of ceramic material 52, 54, 56 and 58. Ceramic body 50, like third ceramic layer 42, has a plurality of electrically conductive leads 60 and 62 formed thereon. Conductive leads 60 and 62 are electrically coupled to coils 36 and 38 respectively, through a plurality of vias, formed through ceramic bodies 42, 12 and 34. In this way, electrical contact can be made between coils 36 and 38, for example, and a processing means (not shown).

Each of the ceramic layers illustrated hereinabove with respect to the FIG. 1 is fabricated of one or more ceramic materials selected from the group consisting of alumina, zirconia and combinations thereof. In one preferred embodiment, each of the layers are fabricated of an alumina/zirconia composite material in which the relative proportion of alumina to zirconia is roughly 3 to 1. Alternatively, the ceramic material may be fabricated with 70 to 30 Vol % alumina and 30 to 70 vol % yttria stabilized zirconia (3 mole % $Y_2O_3$). The primary considerations for selection of a material include the need for an insulating substrate with good thermal shock resistance and the need to shrinkage match to the $Y_2O_3$ stabilized zirconia material. 8 mole % $Y_2O_3$ stabilized zirconia material is a good ionic conductor at 700° C., and is needed for building the oxygen pump and oxygen sensor portions as described hereinbelow. Its properties can be enhanced, particularly as they relate to electrical crosstalk, by separating the conductor elements from the zirconia layer with a thin insulating material. Such ceramic materials may be fabricated from any of a number of known processes.

In operation, the two heating coils 16 and 18 and the two conductive coils 36 and 38 are connected in a Wheatstone bridge arrangement. The coil 36 with no catalyst coating acts as the reference and the other coil 38 with a catalyst coating acts as the sensor. When auto exhaust gases containing hydrocarbons, carbon monoxide and hydrogen come into contact with coil 38, which is kept at 600° to 700° C. operating temperature, they will be oxidized on the catalyst surface forming $CO_2$ and $H_2O(g)$. The heat generated during the catalytic oxidation of the exhaust gases will slightly raise the temperature of the sensor element compared to the reference element. This change in temperature causes a change in resistance of the sensor element from the base line value of $R_o$ to $R_x$, described by the relation $R_x = R_o (1+x)$, where x is the fractional change in resistance. When this sensor is connected in a Wheatstone bridge circuit, the change in sensor resistance causes an imbalance in the Wheatstone bridge circuit. When the bridge is balanced, Vout=0, so:

$R_o/R_{heater2} = R_{reference}/R_{heater1}$

In the unbalanced mode, when the resistance changes are small, $V_{out} = V_{ref}/2*(1-1(1-x/2))$ or approximately, $V_{out} = x^* V_{ref}/4$. The output from this bridge can be processed further, for example, amplified using a single differential op-amp to amplify the voltage signal.

Figure 2:
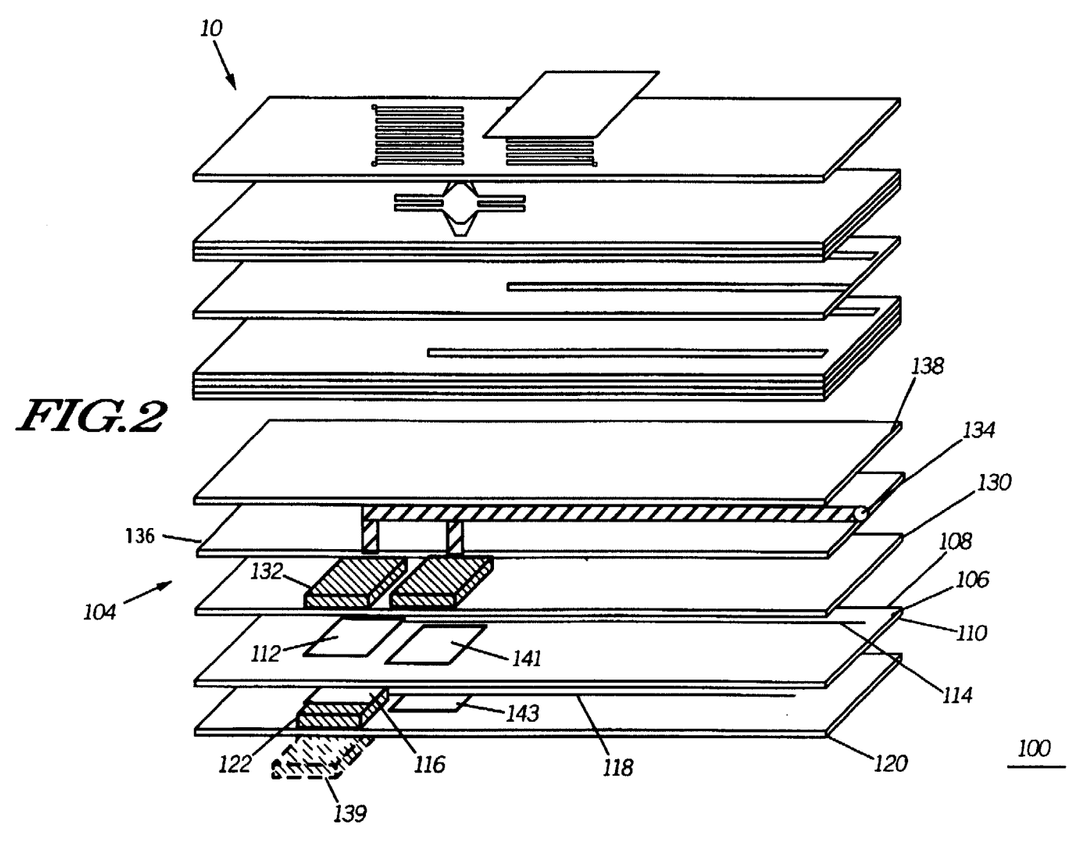
FIG. 2 is an exploded perspective view of an integrated combustion oxygen sensor in accordance with the instant invention.

Referring now to FIG. 2, there is illustrated therein an exploded perspective view of an integrated exhaust gas sensing device in accordance with the instant invention. The integrated exhaust gas sensing device 100 includes a combustion calorimetric sensor 10, as described hereinabove with respect to FIG. 1. Disposed immediately subjacent the calorimetric combustion sensor is an oxygen sensor 104 which will be described in greater detail herein. The oxygen sensor 104 includes a ceramic spacing layer 106 which includes first and second major surfaces 108 and 110. On the first major surface 108 is disposed a reference electrode 112 and an electrically conductive lead 114 for effecting electrical communication between the reference electrode 112 and, for example, a current source or a processing means (not shown). Disposed on the second major surface 110, is a measuring electrode 116 which likewise includes an electrically conductive lead 118 for electrically coupling the measuring electrode with a processing means. Both electrodes 112 and 116 as well as conductive leads 114 and 118 are fabricated of electrically conducting materials such as those described hereinabove with respect to the conducting layers in the calorimetric combustion sensor. The measuring electrode is sandwiched between ceramic layer 106 and ceramic layer 120, but is exposed to exhaust gases through via 122 formed through ceramic layer 120. Accordingly, the integrated exhaust gas sensor is inserted into the flow of exhaust gas so that exhaust gases may surround and be detected by the sensor.

Disposed immediately adjacent and atop of reference electrode 112 is another layer of ceramic layer 130 which has a via 132 formed therethrough. Via 132 is operatively disposed adjacent reference electrode 112 so as to provide a cavity into which a reference atmosphere can be introduced. The reference atmosphere is ambient air which is provided to cavity 132 via a cavity channel 134 formed through another layer of ceramic material 136 disposed immediately atop layer 130. The cavity channel is formed through layer 136 in a manner well known in the art. An additional layer of ceramic material 138 may be disposed atop layer 136 in order to assure that a reference atmosphere is directed through the cavity channel without loss. Each of the layers of ceramic material described herein with respect to oxygen sensor 104 will be fabricated of one or more of the ceramic materials described hereinabove with respect to combustion calorimetric sensor 102. Each of the ceramic layers in oxygen sensor 104 are preferably fabricated of magnesia, calcia or yttria stabilized zirconia.

In another embodiment of the device, a porous layer 139 (in phantom) is deposited on top of the measuring electrode 116. A cavity is created on top of the reference electrode but instead is not connected to the outside atmosphere, via channel 134. Instead the cavity is connected through vias extended to the calorimetric sensor. In addition to the oxygen sensor electrodes 112 and 116, two additional electrodes 141 and 143 can be deposited on either side of layer 106. The electrodes 141, 143 function as an electrochemical oxygen pump, transporting oxygen from the outside exhaust gas atmosphere to the inside cavity, which is connected through vias to the calorimetric sensor.

Figure 3:
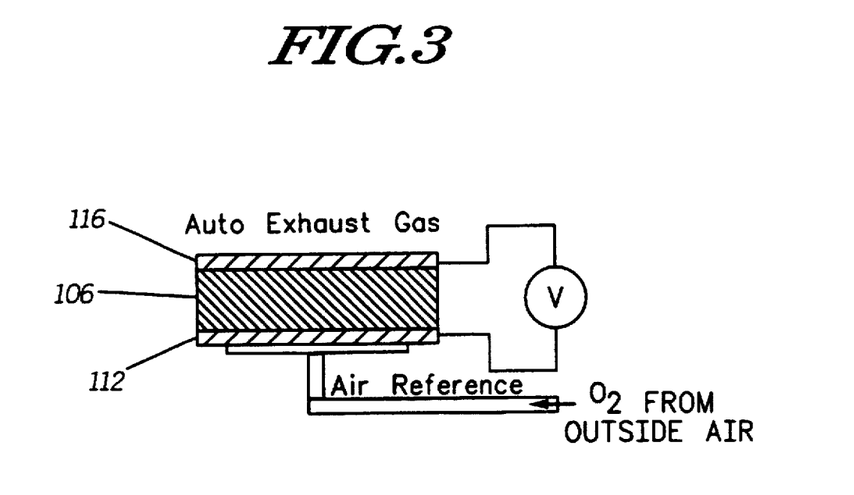
FIG. 3 is a simplified schematic representation of an oxygen sensor such as that illustrated in FIG. 2 operating in the potentiometric mode.

In operation, the calorimetric sensor described hereinabove with respect to FIG. 2 works exactly as that illustrated in FIG. 1. The oxygen sensor described in FIG. 2 works according to the following method. The oxygen sensor is an electrochemical sensor which operates either in the potentiometric mode or in the amperometric mode. A simplified version of the sensor operating in the potentiometric mode is shown in FIG. 3. It consists of a stabilized (with yttria, magnesia or calcia) zirconia solid ceramic electrolyte layer such as layer 106 of FIG. 2 coated with a platinum electrode metal on both sides, i.e., electrodes 112 and 116. Zirconia is an oxygen ion conductor at high temperatures (i.e., 600°–700° C.). When different oxygen partial pressures ($PO_2$) are maintained across the zirconia electrolyte, oxygen ions will flow from one electrode (high $PO_2$ side) to the another (low $PO_2$ side) due the chemical potential difference. This creates a potential difference on both sides of the zirconia cell that can be measured. In the oxygen sensor application, one side of the electrode is exposed to the exhaust gas atmosphere to be measured and the other side is exposed to a reference gas with known oxygen partial pressure such as atmospheric air.

Emf of this cell is given by the Nernst relation:

$$E = RT/4F \ln (PO_2 \text{ air}/PO_2 \text{ gas})$$

Where R is the gas constant; F is the Faraday constant; T is the operating temperature (600°–700° C.); $PO_2$ air is known, and by measuring the voltage signal, oxygen partial pressure of the exhaust gas can be calculated. In auto applications, the stoichiometric point of air/fuel ratio (14.7) is defined as lambda=1. In a rich air/fuel mixture there is more fuel and less air, and the $O_2$ partial pressure in the exhaust is low, generating a high voltage signal, i.e., close to 900 millivolts (mV). In a lean mix, there is more air, and the $O_2$ partial pressure difference is small; thus, the signal is small, i.e., about 100 mV.

Figure 4:
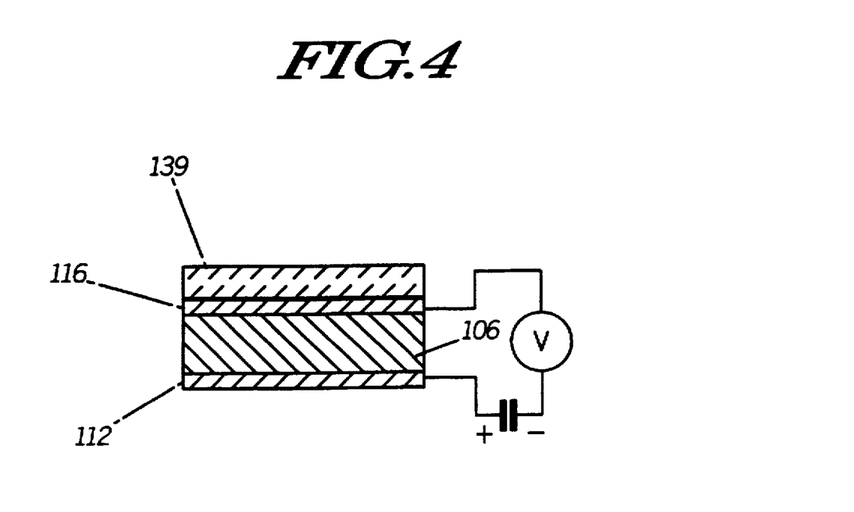
FIG. 4 is a simplified schematic representation of an oxygen sensor such as is illustrated in FIG. 2, operating in the amperometric mode.

In the amperometric mode, illustrated in FIG. 4, a small bias is applied to the electrodes across the zirconia electrolyte, and one electrode surface, the cathode, is covered with porous diffusion layer 139. Without the porous layer, the voltage-current relationship for such a cell shows an increasing current (ionic current) with the increase in applied bias due to the flow of oxygen ions. With a porous diffusion layer covering the cathode surface, depending on the oxygen partial pressure, the current through the sample saturates, because the ionic current is diffusion limited. At high voltages, a large increase in current is observed due to the breakdown of the dielectric and due to the contribution of the electronic current. Once such information is obtained (or calibrated for a given diffusion barrier) then by applying a little bias to the cell, a linear oxygen sensor can be built. In this case there is no need to build an air reference cavity to bring in outside air as shown for the oxygen sensor operating in the potentiometric mode. The advantage of this particular configuration is the oxygen gas generated during the operation of the linear oxygen sensor can be used to burn off the carbon deposits near the calorimetric sensor. An additional oxygen pump could be added if more oxygen is needed for this purpose.

It is to be understood that while only two such devices are illustrated with respect to FIG. 2, a plurality of exhaust gas sensors could be operatively disposed in a multi-layered ceramic material so as to detect the presence of numerous different exhaust gases in the exhaust system of an automobile. Accordingly, and referring now to FIGS. 5, 6, and 7, there is illustrated therein respectively exploded perspective, top and bottom plan views of an integrated multilayered ceramic sensor for monitoring a plurality of different compounds in automobile exhaust gas. For example, in FIG. 5, there is illustrated an exploded perspective view for an integrated multilayered ceramic sensor for monitoring auto exhaust gas. The integrated sensor illustrated in FIG. 5 includes the total combustion calorimetric sensor 10 of FIGS. 1 and 2, as well as the electrochemical oxygen sensor 104 of FIG. 2. The device of FIG. 5 200 further includes a temperature sensor 202, a hydrogen gas sensor 206, an $NO_x$ sensor 208 and a carbon monoxide sensor 210. Each of sensors 206–210 operate in a manner substantially similar to that for the $O_2$ sensor 104, in that electrodes are placed on opposite surfaces of a ceramic layer which ceramic layer acts as an electrolyte for facilitating ion transport between the electrodes. On one side of the ceramic electrolyte layer is provided a cavity adjacent to an electrode, into which a reference gaseous medium, i.e., ambient air, is disposed. The opposite electrode is exposed to exhaust gas, either directly or via a catalyst in order to measure for one or more components in the exhaust gas stream. The temperature sensor 202 may be a thermistor fabricated of, for example, platinum or an alloy of platinum, or an oxide of manganese-cobalt-nickel-ruthenia. The temperature sensor 202 may likewise be fabricated of a plurality of different ceramic layers disposed one atop the other. Preferred ceramic materials for use in fabricating the calorimetric sensor and the temperature sensor include, for example, alumina, zirconia, or an alumina/zirconia composite.

Figure 5:
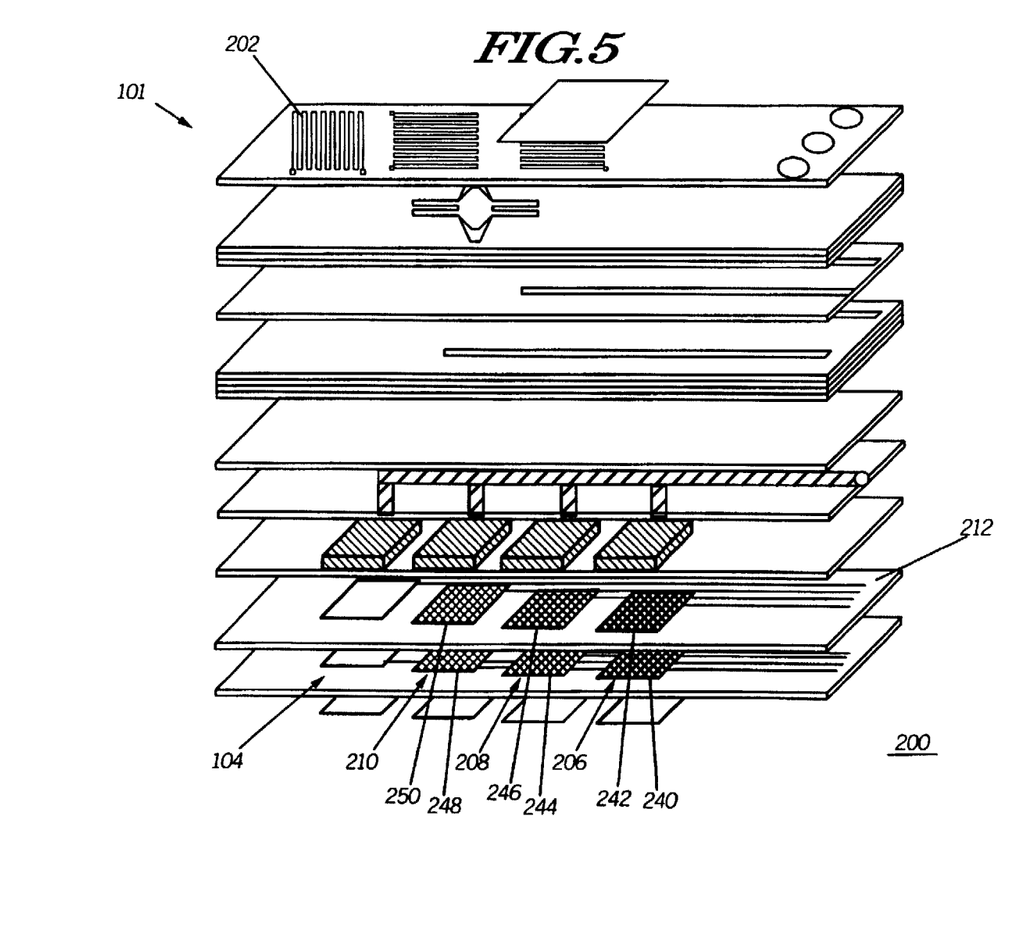
FIGS. 5–7 illustrate, respectively, an exploded perspective, a top plan, and a bottom plan view of a multilayer ceramic integrated sensor for monitoring auto exhaust gasses, in accordance with the instant invention.
Figure 6:
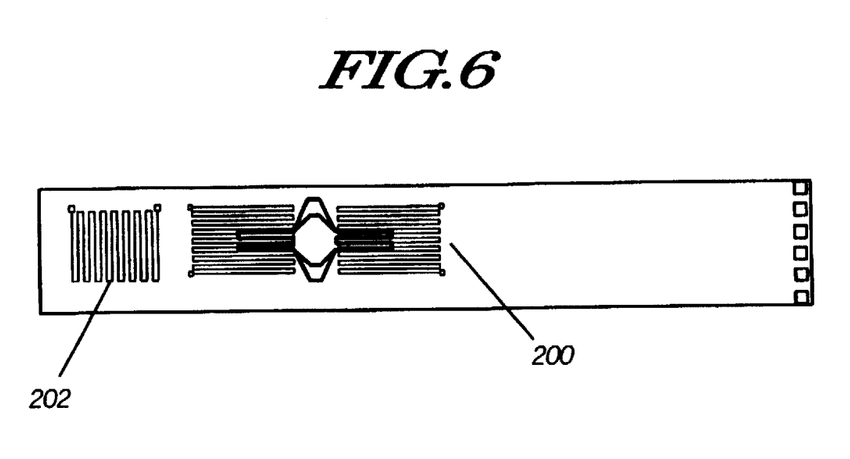
Figure 7:
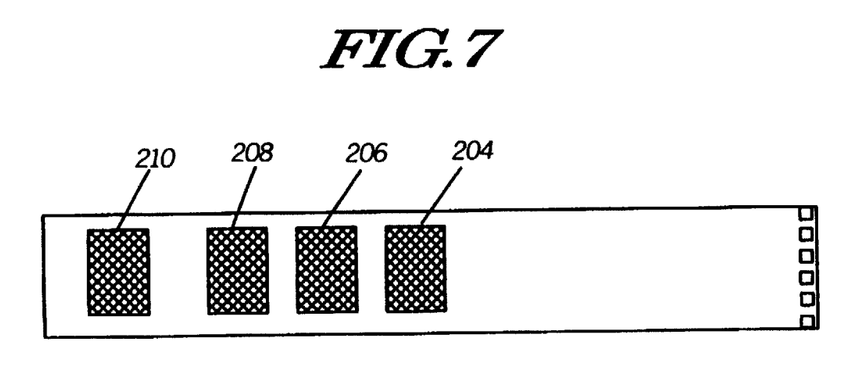

Likewise, in FIG. 5 and in the bottom plan view of FIG. 7 is illustrated a number of different sensing devices. The oxygen sensor is as described hereinabove with respect to FIG. 2. Similarly, the hydrogen gas sensor 206 may be fabricated by depositing a copper oxide 240 and zinc oxide 242 electrodes on opposite sides of a ceramic layer 212. The resulting electrochemical reaction when such device is exposed to hydrogen in the exhaust gas (as compared to ambient air on the counter electrode) will provide an accurate measure of the amount of hydrogen in the exhaust gas.

The $NO_x$ sensor 208 may likewise be provided by depositing lanthanum chromate, lanthanum manganate, or lanthanum ruthenia electrodes 244, 246 on opposite sides of the ceramic substrate. Once again, an electrochemical reaction wherein an oxygen ion is conducted through the, for example, lanthanum chromate electrodes to detect the presence of $NO_x$ type gases in the exhaust stream. Finally, a carbon monoxide sensor 210 may be provided by depositing copper oxide and zinc oxide electrodes 248, 250 on opposite sides of an alumina substrate in a manner similar to that described hereinabove with respect to the hydrogen sensor 206.

Each of the sensor devices may be incorporated into an integrated exhaust gas sensor simply by adding additional layers of ceramic material. Sensors 206, 208 and 210 are all electrochemical sensors, and are built using a configuration similar to that described hereinabove with respect to the O$_2$ sensor. However, in each case, a specific catalyst material will be used with a particular gas which is to be detected. These sensors can be fabricated to operate in either a potentiometric or an amperometric mode as described hereinabove with respect to the oxygen sensor. The important consideration is to select a suitable catalyst material which will oxidize the gaseous species to be detected. For example, in a carbon monoxide sensor, the catalyst will oxide the carbon monoxide to carbon dioxide. This process will reduce the amount of available oxygen near the electrode and correspondingly the voltage signal will change. By comparing this changed signal with a reference signal, or by using a previous calibration and a different parts per million level of carbon monoxide, the amount of carbon monoxide can be determined.

The NO$_x$ and hydrogen gas sensors work in a similar manner. To integrate all of these sensors into a single unit, one need not necessarily add additional layers of ceramic material to the device. Each of the sensors use substantially the same configurations with only different electrode materials deposited. Accordingly, fabrication of the device is simple and highly repeatable. The sensors are simply spaced apart from one another on a single layer of, for example, zirconia. Each of the sensors require a reference atmosphere, such as that described with respect to the O$_2$ sensor above; hence, each can use the same air reference channel, branching off to different sensor areas. This is illustrated in FIG. 5.

When these devices are configured as shown in FIGS. 2 and 4, there is no need to provide the outside air reference, instead all devices operate in the amperometric mode. The oxygen generated during the operation will be transported to the calorimetric sensor for complete combustion and to burn off carbon deposits.

Another advantage of building several gas sensors along with the oxygen sensor on the same layer is the oxygen sensor data provides the base line reference data for easier calibration of the various gas sensor. If during the operation of the sensor if the baseline shifts, it can be easily detected from the oxygen sensor measurements and can be compensated for the other gas sensor measurements.

Figure 8:
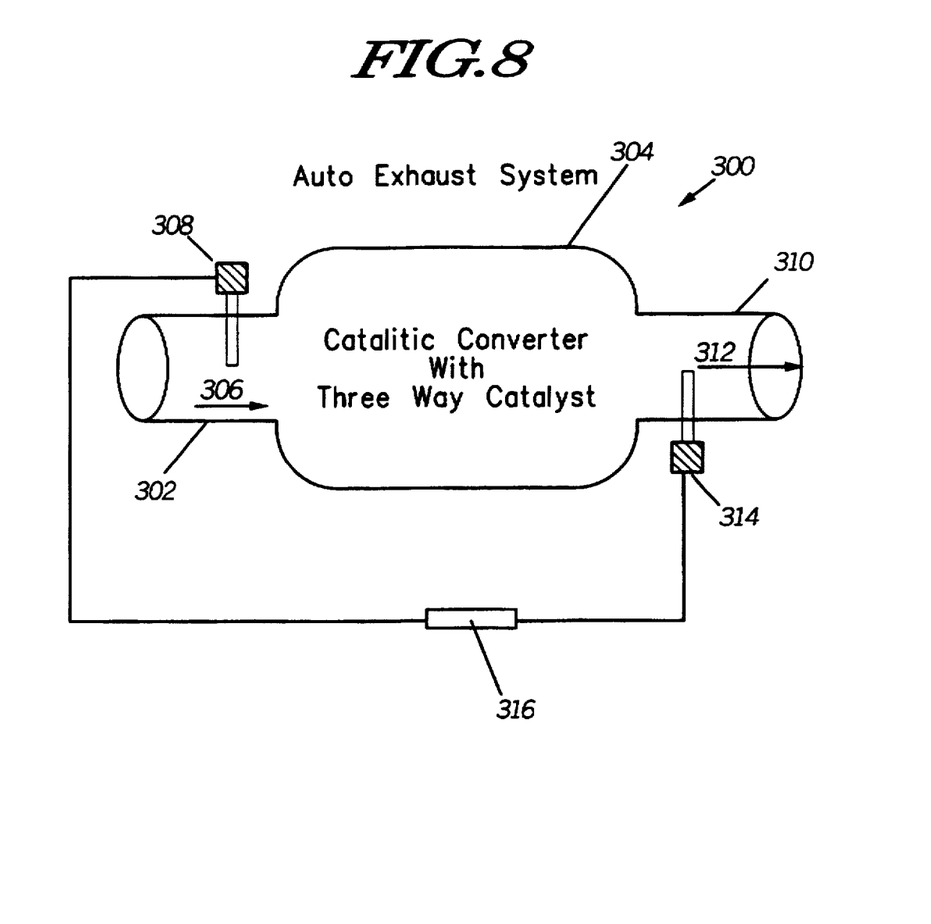
FIG. 8 is a schematic representation of an auto exhaust monitoring system, employing ceramic integrated sensors, in accordance with the invention.

Referring now to FIG. 8, there is illustrated therein an automobile exhaust gas sensing system employing integrated multilayered ceramic combustion sensors in accordance with the instant invention. The exhaust system 300 comprises a first exhaust pipe portion 302 which links the catalytic converter 304 of a conventional automobile with the internal combustion engine (not shown). Exhaust gases from the engine are directed down the exhaust pipe 302 towards the converter 304 in the direction of arrow 306. Exhaust gases accordingly pass over an upstream auto exhaust sensor 308 such as that described hereinabove, with respect to FIGS. 2–7. Sensor 308 provides a reference measure of the amount of various types of components in the exhaust gas prior to entering the catalytic converter 304.

A second exhaust pipe portion 310 links the catalytic converter with ambient air. Exhaust gases exit the catalytic converter 304 in the direction of arrow 312, passing over downstream exhaust gas sensor 314. Exhaust gas sensor 314 measures for the relative amounts of various components in the exhaust gas after exiting catalytic converter 304. The results of the measurement of the gases both upstream and downstream of the catalytic converter are then passed to a processor 316 for comparison. Using the information detected by sensors 308 and 314, the processor 316 can determine the efficiency of the catalytic converter as well as the efficiency of the internal combustion engine upstream of the converter. This information can be used to monitor the engine performance thereby changing the air to fuel ratio or other performance characteristics of the engine so as to optimize performance, and minimize exhaust emissions.

In summary, the multilayer ceramic technology and the layered feature of the structure allows one to combine the zirconia solid electrolyte layers along with an insulating layer to build an integrated sensor which combines an oxygen sensor, CO, NO$_x$ and H$_2$ electrochemical sensors and an oxygen electrochemical pump (if needed) along with a temperature sensor and a calorimetric sensor in one unit. The advantage of this sensor includes using, the oxygen generated during the operation of the electrochemical gas sensors to vent through the structure to the calorimetric sensor to help in complete combustion of the hydrocarbons and to reduce carbon deposits. The presence of the oxygen sensor on the same layer along with the CO, NO$_x$ and H$_2$ sensors, helps in calibrating the baseline data for the gas sensors. In addition, the temperature sensor also helps in calibrating the electrochemical sensors, because the conductivity of the zirconia electrolyte is very much dependent on the operating temperature, which inturn influences the current and the signal level. The temperature sensor also provides useful information about the operating conditions of the auto engine, which influences the constituents of the auto exhaust gas. For example, at low operating temepratures more hydrocarbons are emitted and at higher temperatures less hydrocarbons are emitted but the amount of Nox increases. Thus the sensor under the current invention provides a more comprehensive information about the auto exhaust gases.

While the preferred embodiments of the invention have been illustrated and described, it will be clear that the invention is not so limited. Numerous modifications, changes, variations, substitutions and equivalents will occur to those skilled in the art without departing from the spirit and scope of the present invention as defined by the appended claims.

What is claimed is:

1. multilayered ceramic combustion calorimetric sensor for measuring heat produced as a result of oxidation of hydrocarbons, carbon monoxide, and hydrogen in exhaust gases comprising:
   a first ceramic layer having first and second major surfaces and having a first metallized pattern disposed said first major surface;
   a second ceramic layer having third and fourth major surfaces, and first and second metallized coils formed on said third major surface, wherein said second ceramic layer is operatively disposed atop said first major surface of said first ceramic layer so that said fourth surface of said second layer is adjacent said metallized pattern on said first major surface of said first ceramic layer; and
   a layer of a catalytic material disposed on at least one of said first and second metallized coils wherein hydrocarbons, carbon monoxide, and hydrogen present in said exhaust gases are oxidized by said catalytic material layer to form carbon dioxide and water;
   wherein said metallized pattern, coils, and said catalytic material disposed on said first and second ceramic layers, define said combustion calorimetric sensor.

2. multilayered ceramic combustion calorimetric sensor as in claim 1 further including a third ceramic layer having a second metallized pattern disposed thereon, said third ceramic layer being disposed subjacent to said second major surface of said first ceramic layer and opposite said second ceramic layer, said second metallized pattern being electrically coupled to said first metallized pattern.

3. A multilayered ceramic combustion calorimetric sensor as in claim 2 wherein said ceramic layers each comprises a plurality of ceramic sub-layers.

4. A multilayered ceramic combustion calorimetric sensor as in claim 1, wherein said ceramic layers are fabricated of a $ZrO_2/Al_2O_3$ composite material.

5. A multilayered ceramic combustion calorimetric sensor as in claim 1, wherein said catalyst material is fabricated of platinum or a platinum alloy.

6. An integrated, multi-layered ceramic exhaust gas sensor, including at least a combustion calorimetric sensor for measuring heat produced as a result of oxidation of hydrocarbons, carbon monoxide, and hydrogen in exhaust gases and an oxygen sensor for measuring oxygen partial pressures in said exhaust gases, said exhaust gas sensor comprising:

a first ceramic layer having a first metallized pattern disposed thereon;

a second ceramic layer having first and second major surfaces, and first and second metallized coils formed on said first major surfaces, said metallized coils operatively disposed above said metallized pattern;

a layer of a catalyst material disposed on at least one of said metallized coils wherein hydrocarbons, carbon monoxide, and hydrogen present in said exhaust gases are oxidized by said catalyst material layer to form carbon dioxide and water;

a third ceramic layer having a channel formed through a third major surface, said channel providing a means for introducing an oxygen containing reference gas of known partial pressure to said oxygen sensor in order to measure the oxygen partial pressure of said exhaust gases; and a fourth ceramic layer having a cavity formed therein, said cavity being operatively disposed adjacent an opening in the channel formed through said third ceramic layer wherein said cavity receives the oxygen containing reference gas from said channel;

wherein said first metallized pattern, said first and second metallized coils, and said layer of catalyst material, disposed upon said first and second ceramic layers, define said combustion calorimetric sensor, and said third and fourth ceramic layers define said oxygen sensor.

7. An integrated, multi-layered ceramic exhaust gas sensor as in claim 6, further including at least a fifth ceramic layer disposed subjacent said first and second ceramic layers, said fifth ceramic layer having electrical conductors disposed thereon.

8. An integrated, multi-layered ceramic exhaust gas sensor, as in claim 6, further including at least a sixth ceramic layer disposed subjacent said third and fourth ceramic layers, said sixth ceramic layer having electrical conductors disposed thereon.

9. An integrated, multi-layered ceramic exhaust gas sensor as in claim 6, wherein said first, second, third, and fourth ceramic layers are formed of a material selected from the group of alumina, zirconia, yrttria, and combinations thereof.

10. An integrated, multi-layered ceramic exhaust gas sensor as in claim 6, wherein said catalyst material is fabricated of platinum or a platinum alloy.

11. A multilayered ceramic combustion calorimetric sensor for measuring heat produced as a result of oxidation of hydrocarbons, carbon monoxide, and hydrogen in exhaust gases comprising:

a first ceramic layer having first and second major surfaces and having a first metallized pattern disposed on said first major surface;

a second ceramic layer, disposed atop said first major surface of said first ceramic layer, and having third and fourth major surfaces, and first and second metallized coils formed on said third major surface, and a layer of a catalytic material disposed on at least one of said first and second metallized coils wherein hydrocarbons, carbon monoxide, and hydrogen present in said exhaust gases are oxidized by said catalytic material layer to form carbon dioxide and water; and a third ceramic layer having a second metallized pattern disposed thereon, said third ceramic layer disposed subjacent to said second major surface of said first ceramic layer and opposite said second ceramic layer, and said second metallized pattern being electrically coupled to said first metallized pattern;

wherein said metallized pattern, coils and catalytic material define said combustion calorimetric sensor.

12. A multilayered ceramic combustion calorimetric sensor as in claim 11, wherein said second ceramic layer is operatively disposed atop said first ceramic layer so that said third surface of said second layer is adjacent said metallized pattern on said first ceramic layer.

13. A multilayered ceramic combustion calorimetric sensor as in claim 11 wherein said ceramic layers each comprises a plurality of ceramic sub-layers.

14. A multilayered ceramic combustion calorimetric sensor as in claim 11, wherein said ceramic layers are fabricated of a $ZrO_2/Al_2O_3$ composite material.

15. A multilayered ceramic combustion calorimetric sensor as in claim 11, wherein said catalyst material is fabricated of platinum or a platinum alloy.

* * * * *